United States Patent
Kestone et al.

(10) Patent No.: US 10,318,928 B1
(45) Date of Patent: Jun. 11, 2019

(54) COMPUTERIZED CONTEMPORANEOUS PROCESS CONTROL AND QUALITY ASSURANCE

(71) Applicant: Clear Protocol, Inc., Santa Monica, CA (US)

(72) Inventors: Ernest Michael Kestone, Los Angeles, CA (US); Marie De Lourdes Kestone, Los Angeles, CA (US)

(73) Assignee: Clear Protocol, Inc., Santa Monica, CA (US)

( * ) Notice: Subject to any disclaimer, the term of this patent is extended or adjusted under 35 U.S.C. 154(b) by 150 days.

(21) Appl. No.: 15/205,733

(22) Filed: Jul. 8, 2016

Related U.S. Application Data

(60) Provisional application No. 62/198,081, filed on Jul. 28, 2015.

(51) Int. Cl.
| | |
|---|---|
| *G06Q 10/10* | (2012.01) |
| *G06Q 10/08* | (2012.01) |
| *G08B 21/02* | (2006.01) |
| *G16H 40/20* | (2018.01) |

(52) U.S. Cl.
CPC ......... *G06Q 10/109* (2013.01); *G06Q 10/087* (2013.01); *G08B 21/02* (2013.01); *G16H 40/20* (2018.01)

(58) Field of Classification Search
CPC .................. G06Q 10/109; G06Q 10/1091
USPC ................ 705/1.1, 7.11, 7.12, 7.13, 7.15
See application file for complete search history.

(56) References Cited

U.S. PATENT DOCUMENTS

| | | | |
|---|---|---|---|
| 2008/0140444 A1* | 6/2008 | Karkanias | G06Q 10/02 705/2 |
| 2010/0218132 A1* | 8/2010 | Soni | G06F 19/3418 715/771 |
| 2013/0006671 A1* | 1/2013 | Hufford | G06Q 10/0639 705/3 |

\* cited by examiner

*Primary Examiner* — Igor N Boissov
(74) *Attorney, Agent, or Firm* — Esplin & Associates, PC

(57) ABSTRACT

Improved process control systems containing all of the steps of a desired checklist, means for advising the user of the next sequential step to be performed, answering means enabling the user to reply to the message from said advising means, confirming means responsive to a reply from said answering means to confirm that said step has actually been performed, and alarm means requiring a corrective protocol if the reply from said answering means is not positive or if said confirming means finds that said step has not actually been performed.

10 Claims, 2 Drawing Sheets

COMPUTERIZED CONTEMPORANEOUS PROCESS CONTROL AND QUALITY ASSURANCE

RELATED CASES

This invention is disclosed in my provisional-application, No. 62/198,081 filed Jul. 28, 2015.

FIELD OF INVENTION

This invention relates to process control and especially to process control using checklists.

BACKGROUND

Many processes use checklists to ensure that a desired protocol is followed while carrying out the process. These checklists are often quoted in legal proceedings, to prove that the desired protocols have been performed and to avoid charges of negligence. Unfortunately, checklists are often overlooked, in whole or in part, for various reasons, such as forgetfulness, heavy workload, momentary distraction, and the like. Thus, it is often necessary or desirable to be able to prove that a checklist has been performed, properly and entirely. However, in the past there has been no reliable automated computerized way to perform comprehensive checklist verification, together with logging and saving proof. Furthermore, paper-based checklists and manual entry computerized systems are impractical to use away from a desk or fixed workstation. Thus, none of the prior art in process control has been entirely satisfactory.

BRIEF SUMMARY AND OBJECTS OF INVENTION

These disadvantages of the prior art are overcome with the present invention, and improved process control systems are provided which assure and verify that a checklist has been performed properly and completely, thereby reducing occurrences of preventable errors, such as preventable medical errors.

These advantages are preferably attained by providing improved process control systems user programmable to contain all the sequential steps of a desired checklist, means for advising the user of the next sequential step to be performed, answering means enabling the user to reply to the message from the advising means, confirming means responsive to a positive reply from said answering means to confirm that said step has been actually been performed, and alarm means for requiring a corrective protocol if the reply from said answering means is not positive or if said confirming means finds that said step has not actually been performed.

Accordingly, it is an object of the present invention to provide improved process control and quality assurance systems.

An additional object of the present invention is to provide improved process control systems for assuring and verifying that the steps of a checklist have actually been performed.

Another object of the present invention is to provide improved process control systems for assuring and verifying that the steps of a checklist have actually been performed and that they have been performed properly.

A specific object of the present invention is to provide improved process control systems containing all of the sequential steps of a desired checklist, means for advising the user of the next sequential step to be performed, answering means enabling the user to reply to the message from the advising means, confirming means responsive to a reply from said answering means to confirm that said step has been actually been performed, and alarm means requiring a corrective protocol if the reply from said answering means is not positive or if said confirming means finds that said step has not actually been performed.

A further specific object of the present invention is to perform all the functions using wall or ceiling mounted electronic devices throughout the working areas of a facility; and portable or wearable electronics to support a moving worker (such as a doctor doing hospital rounds, or a veterinarian treating animals in the field).

A further specific object of the present invention is to perform all the functions via voice, gesture, or eye activated, electronic devices, in order to support workers who cannot move their hands to a device or divert their attention, such as surgeons.

A further specific object of the present invention while performing process control is to require management to take over until a successful completion, whenever a breach of protocol cannot be corrected by a worker.

A further specific object of the present invention while performing process control, is to have continuous live support on duty, accessible on demand by the worker, or whenever obstacles are encountered. This live support will facilitate access to whatever additional resources the worker may require to complete a protocol.

These and other objects and features of the present invention will be apparent from the following detailed description, taken with reference to the figures of the accompanying drawings.

BRIEF DESCRIPTION OF THE DRAWINGS

A clear understanding of the key features of the invention summarized above may be had by reference to the appended drawing, which illustrates the method and system of the invention, although it will be understood that such drawings depict preferred embodiments of the invention and, therefore, are not to be considered as limiting its scope with regard to other embodiments which the invention is capable of contemplating.

Accordingly.

DETAILED DESCRIPTION OF THE INVENTION

Figure 1:
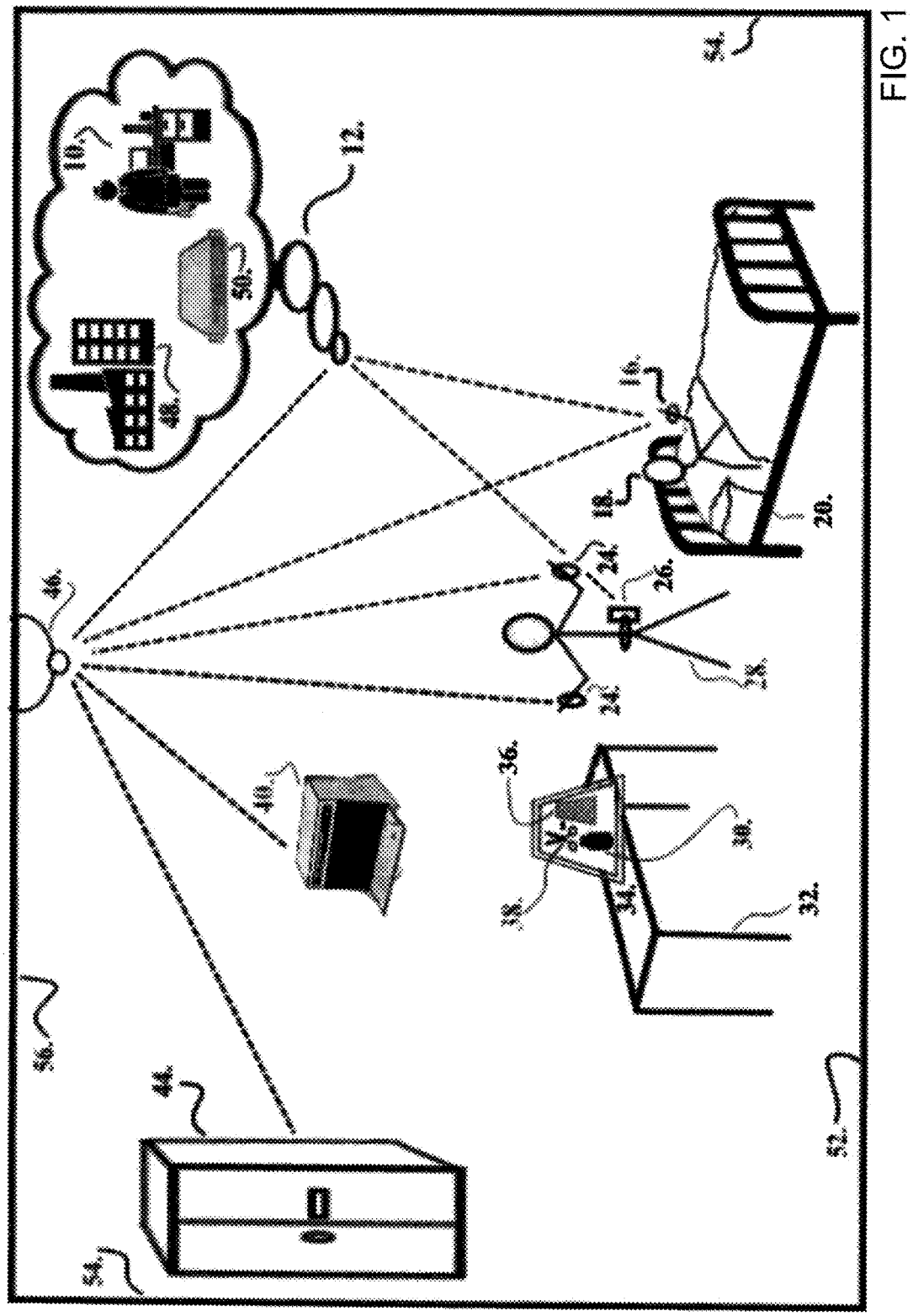
FIG. 1. Shows a diagram of a doctor's office or hospital room, an example of the system being used in healthcare.

In that form of the present invention chosen for purposes of illustration, FIG. 1 shows the system, a combination of software and hardware, being used in a doctor's office or hospital room. Dashed lines signify one-way or two-way communication. Processors and sensors such as a camera, microphone, etc. permanently installed in a ceiling 56 mounted housing 46, portable (not shown) or incorporated into a wearable device 26 (such as a belt), electronic wristbands 24 (these may in some implementations be equipped with Radio-frequency Identification "RFID" and/or Light Detection And Ranging "LIDAR"), image recognition, infrared, sound, means to sense changes in the worker's own electrical capacitance, accelerometer(s), electronic beacons (not shown); and a combination thereof; worker queries may be utilized to continuously track, record, and log into a local storage device(s) 26 and 46 and ultimately into cloud 12 storage 50; movements and positions of persons may be tracked, such as 28 (clinician), and patient 18 lying on bed 20; movements and positions of instruments 38, tools (not shown), machines 40, objects, substances 30 (a bottle of antiseptic), materials 36 (bandage), components (not shown), animals (not shown), and plants (not shown) may be tracked. The location of fixed elements such as the floor 52, walls 54, ceiling 56, and doorways (not shown) will be programmed when setting up the system, so the system can track movements and positions of persons.

The present invention may be programmed to use the current context of different persons such as clinician 28 (e.g., the context may include the proximity to a patient 18, or the proximity to particular equipment such as a sterilizer 40). The system may for example use the context to query the worker (clinician) 28 if they wish to initiate the most likely checklist (for example, the particular checklist out of a library of checklists that is likely to be used with a particular patient, in a particular room, at a particular time, or based on a previous visit/treatment); The system may select or suggest a particular checklist, but a worker may select a different checklist. In some cases, the worker may choose and/or be asked to choose a different checklist from the library, stored on a local server ceiling 56 mounted with other components in a housing 46, or stored into a smartphone (not shown, but in some cases, one or more checklists may be stored in a smartphone), or stored in a wearable device, 26.

When a checklist is selected by the system or by the worker, the system will check and/or verify any prerequisites, such as current professional licensing (e.g., check whether the worker has permission to administer a particular medicine or treatment), training, availability of equipment (e.g., check whether the worker is in the correct room for the selected checklist), availability of supplies and additional personnel, etc. If a check or verification fails or required item(s), such as a particular medical device, are missing, one or more corrective step(s) and/or a corrective protocol will be required prior to initiating the checklist (such as, e.g., request permission to administer the particular medicine or treatment, move to the correct room, obtain the missing required item or particular medical device).

Once the checklist has been selected by the system or by the worker, and the verification of the set of sequential steps included in the checklist is underway, for every individual step the system (by synthesized speech, beeping, or vibration, etc.) requests individual verification from the worker 28, who may respond using gesture or voice. For additional assurance (i.e. additional safeguarding against occurrences of preventable medical errors) during the completion of each step, through sensors such as a camera and microphone, ceiling 56 mounted in a housing 46, portable (not shown) or wearable device 26, supporting information, such as audio, images, video, etc. will be contemporaneously recorded and logged, in a local storage device(s) 26 and 46, and ultimately saved in permanent cloud 12 storage 50. In other words, supporting information, such as contemporaneously recorded audio, images, and/or video, may be used for, e.g., additional assurance to prevent occurrences of preventable medical errors. In some cases, such supporting information may be used at a future time as proof that particular steps occurred during treatment.

If automated sensing (e.g., as may be used to track movements and positions of persons, instruments, medicines, etc., and/or through sensors such as a camera and microphone as may be used to record supporting information) is unavailable or fails, the system will query the worker and obtain specific confirmation such as asking to present a scan code, read a label out loud; etc. For example, such a query may be a request from the system to the worker to present a scan code (for image capture using a camera) or read a label out loud (for audio capture using a microphone).

When any substance or material is in a checklist (i.e. food, feed, medication, chemical, etc.), the system will scan (e.g., through sensors such as a camera, or through proximity-based scanning) identifying elements of containers, and the material itself, such as drugs about to be administered. For example, in some implementations, a drug container may include an RFID tag that identifies the particular drug. The system may scan such an RFID tag through an RFID reader that is included in electronic wristband 24. The system will first confirm such material has been ordered/prescribed (e.g., such a check and/or verification may compare information captured by scanning with information stored in cloud 12 storage 50). For example, the system may compare and/or verify a prescription in an Electronic Medical Record (which may be stored in cloud 12 storage 50) and also query a manufacturer's database 48 to confirm for example, markings on a drug or food approaching a patient (or in proximity of a patient) match the prescription. Components and other manufactured items such as pills, tablets, etc. may be confirmed by shape, size, color, texture, surface shine, imprinting or any other unique features, automatically and by query of the worker. If clarification of a prescribed treatment is needed (e.g., due to a mismatch between information captured by scanning and information included in a stored prescription), the worker and/or the patient may be connected to the doctor's office 10 (e.g., to discuss the mismatch, or to approve any particular difference between the prescribed treatment and the actual treatment the worker is about to administer). For example, a supervisor may approve the use of a different type of medicine, a different dosage, etc. The clinician 28 has reached into a supply cabinet 44 and retrieved supplies: antiseptic 30, scissors 38, gauze 36 and placed them on tray 34 set on table 32, accordingly the system dynamically updated the inventory on the cloud 12 storage 50 to enable resupply, invoicing/billing, internal cost control and other data analysis.

The system will warn of either, an approaching breach of protocol (e.g. a worker reads a particular dosage out loud and the particular dosage does not match the dosage in the prescription, or sterile equipment approaches a contaminated surface, or the wrong equipment or medical device is in close proximity to the patient, etc.), incorrect assembly, incorrect type of a drug, incorrect amount of a drug, incorrect material about to be used, or incorrect tool about to be used. Some types of breaches of protocol can only be detected after the breach has already occurred, but other types of breaches of protocol may be detected before they occur.

A breach of protocol (either an approaching breach or a breach that has already occurred) will initiate one or more corrective subroutines and/or a corrective protocol, leading to resumption of the initial task and/or original checklist. For example, an incorrect dosage may be corrected (before administering) or counteracted (after administering), a contaminated surface may be sterilized, the correct equipment or medical device may be obtained, etc., and after one or more corrective steps and/or a corrective protocol, the initial task and/or original checklist may be resumed.

In the event of a breach of protocol (either an approaching breach or a breach that has already occurred) that is not corrected by the worker the system will require management (e.g., a supervisor) to take over the particular medical process associated with the checklist until a successful completion of the checklist. For example, successful completion of a particular checklist may require individual verifications by a user and/or supervisor of the individual steps from a particular set of sequential steps. Each individual verification confirms that an individual step has been performed in accordance with one or more particular protocols (e.g., a default or original protocol and a corrective protocol) for the particular medical process. At the conclusion of the particular set of sequential steps, the particular checklist has been completed successfully.

Confirmation will be obtained for each step, until successful completion of all the steps in the checklist and the protocol is concluded and logged on the cloud 12 storage 50 to enable such things as invoicing/billing, and internal cost control.

Figure 2:
FIG. 2 illustrates a method for determining a checklist has been performed in accordance with a protocol while carrying out a medical process, in accordance with one or more implementations described in this disclosure.

FIG. 2 illustrates a method 200 for determining a checklist has been performed in accordance with a protocol while carrying out a medical process, in accordance with one or more implementations. The operations of method 200 presented below are intended to be illustrative. In some implementations, method 200 may be accomplished with one or more additional operations not described, and/or without one or more of the operations discussed. Additionally, the order in which the operations of method 200 are illustrated in FIG. 2 and described below is not intended to be limiting.

In some implementations, method 200 may be implemented using one or more processors (e.g., a digital processor, an analog processor, a digital circuit designed to process information, an analog circuit designed to process information, a state machine, and/or other mechanisms for electronically processing information). The one or more processors may include one or more devices executing some or all of the operations of method 200 in response to instructions stored electronically on an electronic storage medium. The one or more processors may include one or more devices configured through hardware, firmware, and/or software to be specifically designed for execution of one or more of the operations of method 200.

An operation 202 may include storing a library of checklists in electronic storage. Individual ones of the checklists may include sets of sequential steps that need to be performed properly to complete medical processes in accordance with protocols. Operation 202 may be performed by a component that is the same as or similar to cloud 12 storage 50, in accordance with one or more implementations.

An operation 204 may include selecting an individual checklist from the library. Operation 204 may be performed by a component that is the same as or similar to the processor incorporated into wearable device 26 and/or electronic wristband 24, permanently installed in ceiling 56 mounted housing 46, and/or performed by a user, in accordance with one or more implementations.

An operation 206 may include querying a user whether the user wishes to initiate verification of the individual checklist, the individual checklist including a set of sequential steps that need to be performed properly to complete a medical process in accordance with a protocol. Operation 206 may be performed by a component that is the same as or similar to the processor incorporated into wearable device 26 and/or electronic wristband 24, and/or permanently installed in ceiling 56 mounted housing 46, in accordance with one or more implementations.

An operation 208 may include requesting, responsive to initiation by the user, individual verifications by the user for completions of individual steps from the set of sequential steps. The individual verifications may be requested through one or more of speech, beeping, and vibration. Operation 208 may be performed by a component that is the same as or similar to the processor incorporated into wearable device 26 and/or electronic wristband 24, and/or permanently installed in ceiling 56 mounted housing 46, in accordance with one or more implementations.

An operation 210 may include receiving the individual verifications by the user for the completions of the individual steps from the set of sequential steps. The individual verifications may be received through a wearable device worn by the user that records and logs one or more of audio, images, and video during the completions of the individual steps for assurance the individual checklist has been performed in accordance with the protocol. Operation 210 may be performed by a component that is the same as or similar to the processor incorporated into wearable device 26 and/or electronic wristband 24, in accordance with one or more implementations.

An operation 212 may include determining, based on the received individual verifications, whether the set of sequential steps has been performed in accordance with the protocol. Operation 212 may be performed by a component that is the same as or similar to the processor incorporated into wearable device 26 and/or electronic wristband 24, and/or permanently installed in ceiling 56 mounted housing 46, in accordance with one or more implementations.

An operation 214 may include generating an alert to the user, responsive to a determination that the set of sequential steps has not been performed in accordance with the protocol, and requesting verification by the user that a corrective protocol be performed to remedy that the set of sequential steps has not been performed in accordance with the protocol. Operation 214 may be performed by a component that is the same as or similar to the processor incorporated into wearable device 26 and/or electronic wristband 24, and/or permanently installed in ceiling 56 mounted housing 46, in accordance with one or more implementations.

An operation 216 may include generating a second alert to a supervisory user, responsive to a second determination that the corrective protocol has not been performed. The second alert may be regarding the determination that the set of sequential steps has not been performed in accordance with the protocol and/or regarding the second determination that the corrective protocol has not been performed. Operation 216 may be performed by a component that is the same as or similar to the processor incorporated into wearable device 26 and/or electronic wristband 24, and/or permanently installed in ceiling 56 mounted housing 46, in accordance with one or more implementations.

All the above and other embodiments are possible, depending on the work volume and equipment budget—as well as user productivity and convenience. A single worker out in the field (such as veterinary doctor, appliance repair, utility worker, home caregiver) will be able to utilize his own PC or even a smart phone as a processor/transmitter. For example, a smartphone may be used to perform at least some of the functionality described in this disclosure, in particular if the smartphone includes peripheral sensors.

This invention is expandable in modules to serve facilities of any size.

Obviously, numerous other variations and modifications can be made without departing from the spirit of the present invention. Therefore, it should be clearly understood that the forms of the present invention described above and shown in the figures of the accompanying drawing are illustrative only and are not intended to limit the scope of the present invention.

What is claimed is:

1. A process control system configured to determine a checklist has been performed in accordance with a protocol while carrying out a medical process, thereby reducing occurrences of preventable medical errors, the system comprising:

a computer including one or more processors, a speaker, and electronic storage, wherein the electronic storage contains a set of sequential steps of the checklist, wherein the set of sequential steps needs to be performed properly to complete the medical process, wherein the one or more processors are configured to:

query a user whether the user wishes to initiate verification of the checklist; and responsive to initiation by the user, request individual verifications by the user for completions of individual steps from the set of sequential steps, wherein the individual verifications are requested through one or more of speech, beeping, and vibration;

a wearable device configured to be worn by the user and to enable the user to reply via one or more of voice activation, gesture activation, and eye activation to the requests for individual verifications for the individual steps from the set of sequential steps, wherein the wearable device is further configured to record and log one or more of audio, images, and video during the completions of the individual steps for assurance the checklist has been performed in accordance with the protocol;

wherein the one or more processors are further configured to:

receive the individual verifications by the user for the completions of the individual steps from the set of sequential steps;

determine, based on the received individual verifications, whether the set of sequential steps has been performed in accordance with the protocol;

responsive to a determination that the set of sequential steps has not been performed in accordance with the protocol, generate an alert to the user and request verification by the user that a corrective protocol be performed to remedy that the set of sequential steps has not been performed in accordance with the protocol; and responsive to a second determination that the corrective protocol has not been performed, generate a second alert to a supervisory user regarding the determination that the set of sequential steps has not been performed in accordance with the protocol and/or regarding the determination that the corrective protocol has not been performed.

2. The system of claim 1, wherein the corrective protocol includes performance of a set of sequential steps.

3. The system of claim 1, wherein the wearable device includes a microphone.

4. The system of claim 1, wherein the wearable device includes a camera.

5. The system of claim 1, wherein the wearable device includes sensors for detecting individual completions of the individual steps from the set of sequential steps.

6. The system of claim 1, wherein the wearable device is configured to enable the user to reply by recording the user's verbal answer.

7. The system of claim 1, wherein the user is a clinician, and wherein the alert is generated through an audio-visual alarm.

8. The system of claim 1, wherein the one or more processors are further configured to, responsive to the determination that the set of sequential steps has not been performed in accordance with the protocol, generate an alert to other persons.

9. The system of claim 1, further comprising:

prerequisite verification means, operable after verification of the checklist has been initiated, but before any steps have been performed, to verify that all prerequisites have actually been satisfied.

10. The system of claim 1, wherein the one or more processors are further configured to enable the user to access continuous live support on demand by the user.

* * * * *